United States Patent [19]

Price et al.

[11] 4,278,110

[45] Jul. 14, 1981

[54] DEMAND RESPONSIVE FLOW CONTROLLER

[76] Inventors: Ernest H. Price, 1266 Pepper Dr., El Centro, Calif. 92243; Douglas C. Howard, 3004 Stratford Dr., Chesapeake, Va. 23321

[21] Appl. No.: 93,919

[22] Filed: Nov. 13, 1979

[51] Int. Cl.³ ............................................... F15C 1/12
[52] U.S. Cl. ............................ 137/805; 128/204.24; 128/204.26; 128/207.18; 137/829; 137/DIG. 9
[58] Field of Search ...................... 128/204.24, 204.25, 128/204.26, 205.24, 207.18; 137/805, 829, DIG. 9

[56] References Cited

U.S. PATENT DOCUMENTS

| | | | |
|---|---|---|---|
| 2,868,199 | 1/1959 | Hudson | 128/207.18 |
| 3,368,555 | 2/1968 | Beasley | 128/204.24 |
| 3,446,207 | 5/1969 | Metivier | 128/205.24 |
| 3,486,502 | 12/1969 | Wilson | 128/204.26 |
| 3,537,449 | 11/1970 | Foxwell et al. | 128/204.24 |
| 3,598,116 | 8/1971 | Peters et al. | 128/204.24 X |
| 3,952,740 | 4/1976 | Scurlock | 128/202.22 |
| 4,072,148 | 2/1978 | Munson et al. | 128/204.25 |

*Primary Examiner*—Henry J. Recla
*Attorney, Agent, or Firm*—Dennis T. Griggs

[57] ABSTRACT

A demand responsive flow controller for use in a respiration system for the administration of oxygen from a pressurized source through a cannula to a patient is disclosed. A flow path between the pressurized source and the cannula is opened and closed by a fluidic valve which is responsive to the presence and absence of a low pressure power stream developed by a flow restrictor coupled to the pressurized source. The low pressure power stream is applied to the control port of the on/off fluidic valve by a monostable fluidic switch which conducts the low pressure power stream through the valve control port of the on/off valve in response to expiration by the patient, and which diverts the low pressure power stream away from the on/off valve in response to inspiration by the patient. In a preferred embodiment, the monostable fluidic switch is gate controlled and includes a discharge port through which the power stream is conducted only in response to a respiration signal corresponding with expiration, and an open vent port through which the power stream is conducted only in response to a respiration signal corresponding with inspiration. A fluidic transducer is coupled to the cannula and to the gate controlled port of the monostable fluidic switch for opening and closing the gate control port to ambient pressure in response to inspiration and expiration, respectively.

5 Claims, 3 Drawing Figures

DEMAND RESPONSIVE FLOW CONTROLLER

BACKGROUND OF THE INVENTION

1. Field of the Invention

The invention relates generally to respiration apparatus for administering oxygen to a patient, and in particular to a positive pressure, demand responsive fluidic controller.

2. Description of the Prior Art

Positive pressure respiration systems are used in inhalation therapy for the administration of oxygen and adjuvant gases in the treatment of patients having pulmonary disorders such as asthma or pneumonia. Most conventional respirators are fairly complex and employ a variety of elements including snap valves, springs, solenoid valves, magnets, gear boxes, ratchets, mechanical linkages, pulleys, photocells, electronic circuitry, and other components to provide a number of functions. The complexity and hybrid nature of these systems results in large, heavy and expensive units which are somewhat fragile and liable to mechanical failure.

Positive pressure respiration systems normally fall within two broad classifications, that is, positive pressure volume limited systems and positive pressure flow cut-off or flow limited systems. Positive pressure volume limited respiration systems are distinguishable by the fact that in the use thereof, a predetermined volume of gas is forced into the patient's lungs at predetermined intervals. In positive pressure flow cutoff respiration systems, the patient initiates the flow of gas by slight inspiration, after which the patient is forced to inspire as much of a desired gas, such as oxygen, as his lungs will permit or accept.

In yet another category of positive flow respiration devices, oxygen is continuously delivered at a substantially constant, regulated flow rate to a nasal cannula for inspiration by a patient. In this arrangement oxygen is continuously delivered to the patient at a constant rate during expiration as well as during inspiration. Since the respiration cycle is approximately 30% inspiration and 70% expiration, a substantial amount of oxygen is vented without recovery during expiration. Because the nasal passages are being ventilated constantly, the oxygen must usually be circulated through a humidifier to improve the patient's comfort during the extended administration. These humidifiers represent potent sources of nosocomial (hospital acquired) infections. Additionally, these humidifiers require much staff attention in keeping the water level up and changing systems 2-4 times per day. Furthermore, the accumulation of a large volume of vented oxygen around a patient's bed, especially within a small room, represents a fire safety hazard. Moreover, since the cost of oxygen administration is directly related to the total amount of oxygen delivered to the patient, including that volume of oxygen which is vented rather than being inspired, a substantial percentage of the cost of the oxygen administration service could be saved if some way could be found to substantially reduce or eliminate the venting of oxygen during expiration.

SUMMARY OF OBJECTS OF THE INVENTION

It is, therefore, the principal object of the present invention to provide a demand responsive flow controller for use in a respiration system for the administration of oxygen from a pressurized source through a cannula to a patient.

Another object of the invention is to provide respiration apparatus for administering oxygen to a patient which features a positive pressure, demand responsive fluidic controller which minimizes the venting or loss of oxygen during expiration.

Yet another object of the invention is to provide a positive flow respiration device in which oxygen is delivered at a substantially constant, regulated flow rate to a nasal cannula, the regulated flow being interrupted in response to respiratory excursions by the patient.

SUMMARY OF THE INVENTION

According to novel features of the present invention, the foregoing objects are achieved by a demand responsive flow controller in which a flow path between a pressurized source and a cannula is opened and closed by a fluidic valve which is responsive to the presence and absence of a low pressure power stream developed by a flow restrictor coupled to the pressurized source. The low pressure power stream is applied to the control port of the on/off fluidic valve by a monostable fluidic switch which conducts the low pressure power stream through the valve control port of the on/off valve in response to expiration by the patient, and which diverts the low pressure power stream away from the on/off valve in response to inspiration by the patient.

In a preferred embodiment, the monostable fluidic switch is gate controlled and includes a discharge port through which the power stream is conducted only in response to a respiration signal corresponding with expiration, and an open vent port through which the power stream is conducted only in response to a respiration signal corresponding with inspiration by the patient. A fluidic transducer is coupled to the cannula and to the gate control port of the monostable fluidic switch for producing the respiration signals by opening and closing the gate control port to ambient pressure in response to inspiration and expiration, respectively.

The power stream may be conducted to the vent port in response to inspiration or expiration, depending on whether the fluidic gate valve is normally open or normally closed. The system preferably vents the power stream in expiration to provide fail-safe characteristics in event of failure, i.e., the normally open valve provides continuous flow.

According to an alternate embodiment, the monostable fluidic switch includes a power stream inlet port coupled to the flow restrictor, a vent port through which the power stream is conducted when the vent port is opened to ambient pressure, and a valve actuation port through which the power stream is conducted when the vent port is closed to ambient pressure. In this arrangement, the monostable fluidic switch has an asymmetrical channel structure which provides memory capability in that the fluidic wall attachment of the power jet is stable in relation to one channel only, with switching of the power jet through the other channel being effected by blocking the preferred channel, with the flow reverting to the preferred channel once the preferred channel is unblocked. In this arrangement, a fluidic transducer is coupled to the cannula and to the vent port of the monostable fluidic switch for opening and closing the vent port in response to inspiration and expiration, respectively. Because the vent port is associated with the preferred channel, the power stream is diverted in response to expiration as the transducer blocks the vent port, thereby actuating the fluidic valve to the closed condition and interrupting oxygen flow, and actuating the fluidic valve to the open position as the vent port is opened in response to inspiration, thereby resuming the delivery of oxygen flow to the patient.

The foregoing and other related objects and advantages of the present invention will become more apparent from the following specification, claims and appended drawings wherein:

DESCRIPTION OF THE PREFERRED EMBODIMENTS

Figure 1:
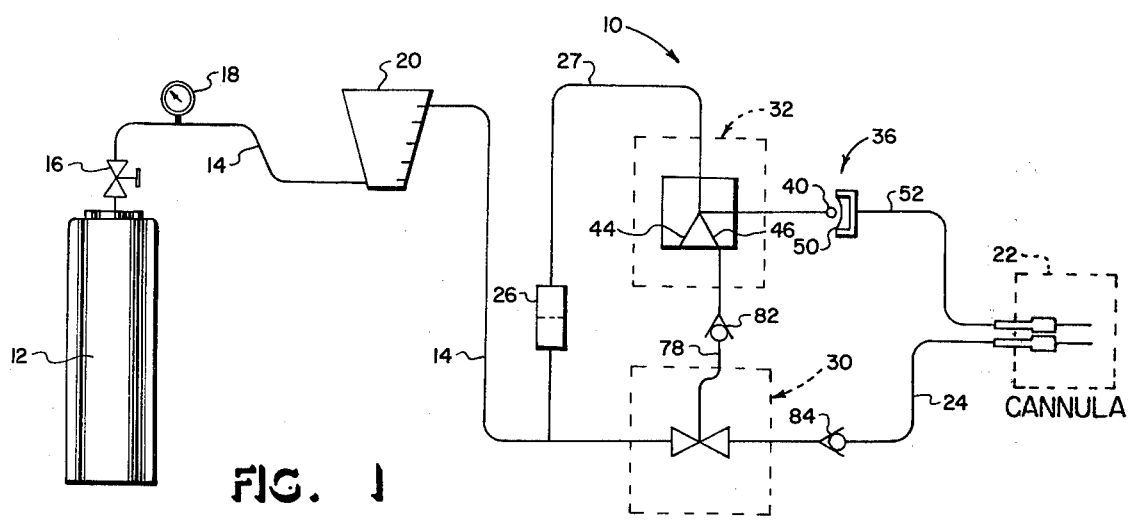
FIG. 1 is a schematic view of a respiration system for the administration of oxygen from a pressurized source through a cannula to a patient which features a demand responsive flow controller constructed according to the teachings of the invention.

In the description which follows, like parts are marked throughout the specification and drawings with the same reference numerals, respectively. The figures are not necessarily drawn to scale and in some instances portions have been exaggerated in order to more clearly depict certain features of the invention.

Referring now to FIG. 1 of the drawings, a demand responsive flow controller 10 constructed according to the teachings of the invention is operably connected to a cylindrical oxygen tank 12 in which a pressurized supply of oxygen is stored. Pressurized oxygen is delivered to the flow controller 10 through a supply conduit 14. The pressure of oxygen delivered through the supply conduit is established by a valve 16 and a gauge 18 in the usual manner. A flow meter 20 controls the rate of flow of the oxygen supplied from the compressed gas cylinder 12.

According to the invention, the flow controller 10 delivers oxygen from the pressurized cylinder 12 through a cannula 22 for inspiration by a patient on a demand basis. That is, the cannula 22 is inserted into the nasal cavities and as the patient inspires, a regulated flow of oxygen is conducted through the flow controller 10 and through a delivery conduit 24. Expiration by the patient is sensed by the flow controller 10 which operates to interrupt the flow of oxygen in response thereto. During the respiration cycle, the flow controller 10 senses the initiation of inspiration and opens a flow path between the supply conduit 14 and the delivery conduit 24 to supply the regulated flow of oxygen to the patient. According to this arrangement, oxygen is supplied on a demand basis only, with the oxygen supply being interrupted during expiration, so that the oxygen is administered only according to the patient's needs, thereby avoiding the substantial oxygen loss associated with continuous delivery respirators.

Figure 2:
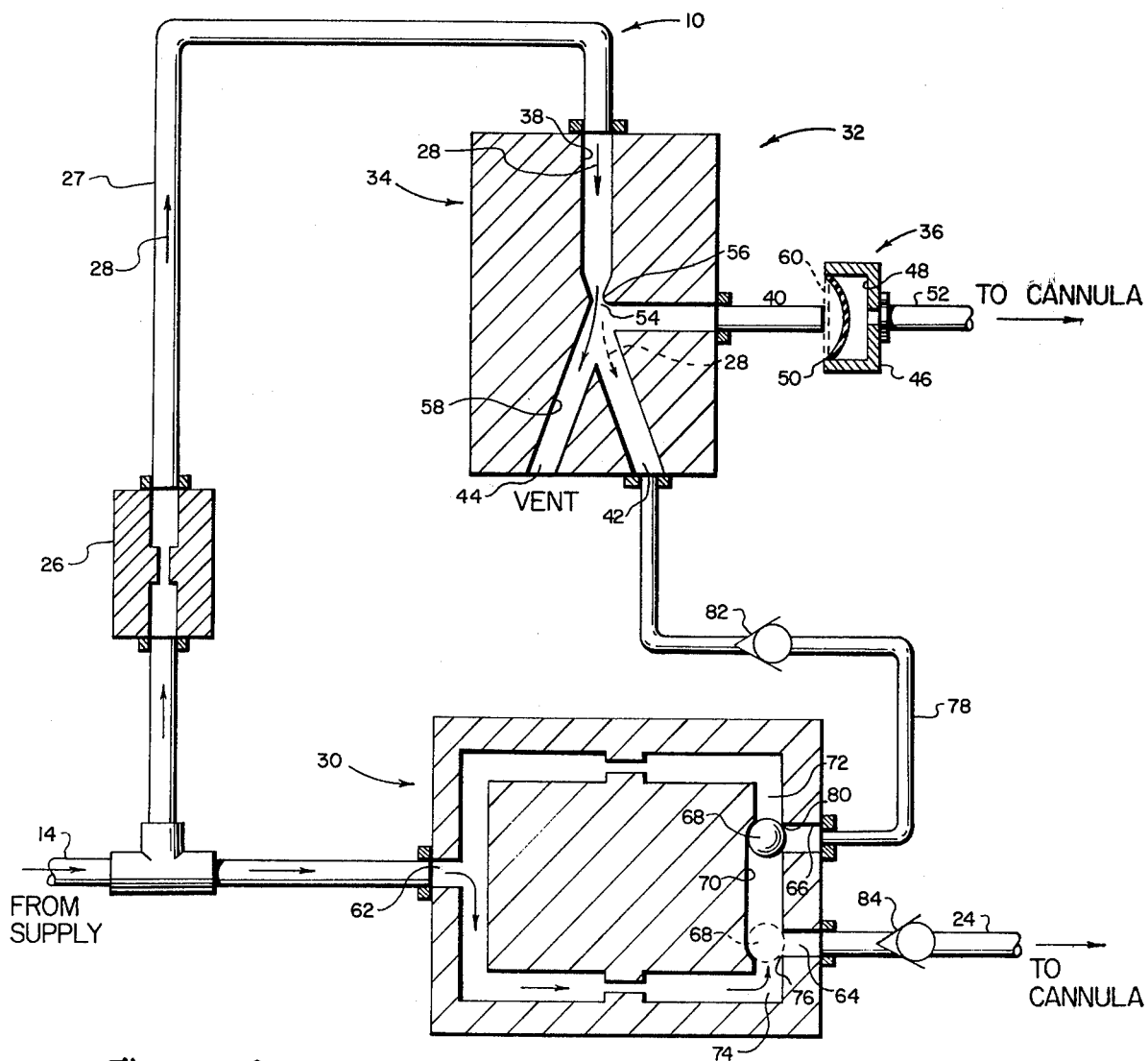
FIG. 2 is a schematic view, partly in section, which depicts the structure of the fluidic components of the demand responsive flow controller shown in FIG. 1.

Referring now to FIGS. 1 and 2, a preferred embodiment of the demand responsive flow controller comprises an orifice flow restrictor 26 coupled to the supply conduit 14 for developing a relatively low volume flow rate power stream 28, for example 0.5 liters per minute for control purposes. A flow path between the oxygen cylinder 12 and the cannula 22 is opened and closed by a fluidic valve 30 which is responsive to the presence and absence of the low pressure power stream developed by the flow restrictor 26 to open and close the flow path. Actuation of the fluidic valve 30 is controlled by a fluidic gate assembly 32 which includes a monostable fluidic switch 34 and a fluidic transducer 36.

According to the preferred embodiment shown in FIG. 2, the monostable fluidic switch 34 includes a power stream inlet port 38 which is coupled to the flow restrictor 26 through a conduit 27 for receiving the power stream 28, a gate control port 40 for receiving a respiration signal, a power stream discharge port 42 through which the power stream is conducted only in response to a respiration signal corresponding with expiration, and an open vent port 44 through which the power stream is conducted only in response to a respiration signal corresponding with inspiration.

The fluidic transducer 36 is coupled to the cannula 22 and to the gate control port 40 for routing the respiration signals for opening and closing the gate control port to expose it to ambient pressure in response to inspiration and expiration, respectively. The fluidic transducer 36 includes a housing 46 enclosing a pressure chamber 48 which is sealed by a resilient, movable latex diaphragm 50. The pressure chamber 48 is connected in fluid communication with the cannula 22 through a sensor conduit 52. As the patient inspires, the sensor conduit 52 induces a relatively low pressure level within the pressure chamber 48 as compared with the surrounding ambient pressure, thereby causing the latex diaphragm 50 to be displaced away from the control port 40, thereby opening the control port and exposing it to atmospheric pressure.

The monostable fluidic switch 34 is characterized by stable flow through the power stream discharge port 42 in the absence of a bias signal. In the asymmetrical arrangement shown in FIG. 2, the power stream 28 will attach to the side wall of the power stream discharge port 42 in the absence of flow through the control port 40. The power stream 28, as it is discharged through the nozzle region 54, is biased toward the power stream discharge port 42 by the rounded corner 56 which forms a boundary for the nozzle region. If sufficient gas flows through the control port 40, or if the pressure within the control port 40 suddenly increases, the low pressure power stream 28 will be deflected or diverted into the vent port 44 and will attach to the side wall 58 according to the Coanda Effect in which a free jet when emerging from a jet nozzle will tend to follow a nearby curved or inclined surface and will become attached thereto and flow along the surface if the curvature or angle of inclination is not too sharp. The Coanda Effect and the principles of operation of fluidic logic devices based upon the Coanda Effect are described in the text *Fluidics*, edited by E. F. Humphrey et al and published by the Fluid Amplifier Associates, Inc., Boston, 1965.

During expiration, the low pressure condition previously produced by inspiration is equalized with ambient pressure, thereby allowing the diaphragm 50 to be displaced into sealing engagement with the vent port 40. The position of the diaphragm which corresponds with sealing engagement with the vent port 40 is indicated by the dashed line 60 in FIG. 2. Stable flow through the power stream discharge port 42 responsive to closure of the vent port 40 is indicated by the dashed arrow 28. When pressure equilibrium is upset by opening the control port 40, the low pressure power stream 28 is deflected through the vent port 44 into the surrounding atmosphere. Because the low pressure power stream volume flow rate is relatively small, for example 0.5 liters per minute, and because venting of the power stream 28 into the atmosphere occurs only during expiration, only a minimal amount of oxygen is lost through the operation of this embodiment.

Upon inspiration, stable flow is interrupted and the power stream 28 is deflected through the vent port away from the fluidic valve 30. Referring again to FIG. 2, the fluidic valve 30 includes an inlet port 62 connected to the supply conduit 14, an outlet port 64 connected to the delivery conduit 24, and a control port 66 connected in fluid communication with the power stream discharge port 42 of the monostable fluidic switch 34. The fluidic valve 30 includes a movable ball 68 which moves in a cylinder 70 in response to relative pressure forces applied to it. When the ball is in the valve open position as illustrated in FIG. 2, the supply pressure is applied to the ball 68 across the area of the upper supply port 72. If the outlet port 64 is unblocked, a pressure drop occurs in the lower supply channel 74. If the pressure in the outlet port 64 is sufficiently low, the total force exerted upon the ball 68 by the pressure in the control port 66 combined with the pressure in the upper supply port 72 will exceed the forces applied by the supply pressure through the lower supply channel 74 and the pressure in the outlet port 64. Since the applied force equals the pressure times the effective area, an appropriate choice of the relative areas of the supply port nozzles and cylinder allows the ball 68 to be held in position. If the pressure in the control port 66 is raised sufficiently, the ball will move to the closed position as indicated by the dashed line and shut off the flow to the outlet port 64. A tight seal between the ball 68 and the power flow nozzle seat 76 is desirable since the valve will switch itself if too much flow leaks around the ball and changes the relative pressure levels. Other fluidic valves, such as a diaphragm actuated bistable valve having a large diaphragm surface area with respect to inlet port area, may be used to good advantage for interrupting the flow of oxygen.

The low pressure power stream 28 is conducted through a control conduit 78 during expiration, forcing the ball into sealing engagement with the power flow nozzle seat 76, and thereby interrupting the flow of oxygen from the supply cylinder to the cannula. During inspiration, the diaphragm is deflected away from the control port 40, thereby causing deflection of the power stream through the vent. Removal of the power stream from the control conduit 78 permits the ball 68 to be displaced into sealing engagement with the upper power flow nozzle seat 80, thereby opening the flow path from the supply conduit 14 through the outlet port 64 to the delivery conduit 24.

A check valve 82 is connected in series fluid circuit relation between the valve control port 66 and the power stream discharge port 42 for eliminating feedback of pressure fluctuations into the monostable switch which might interfere with its operation. Similarly, a check valve 84 is connected in series between the valve outlet port 64 and the cannula 22 in order to isolate the valve 30 with respect to pressure fluctuations caused by inspiration and expiration into the delivery line 24 of the cannula.

Figure 3:
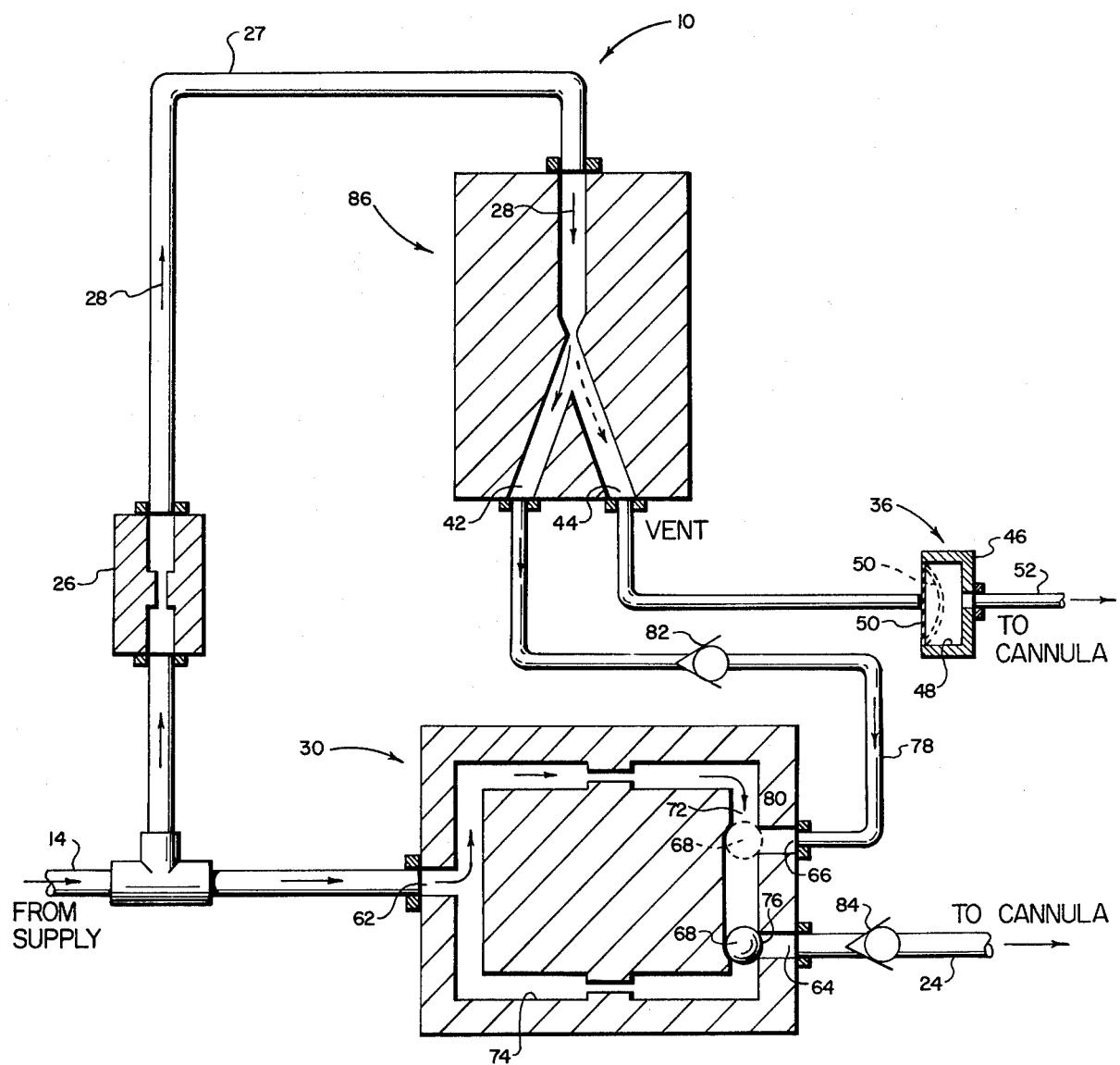
FIG. 3 is a view similar to FIG. 2 which depicts an alternate embodiment of the invention.

Referring now to FIG. 3, an alternate embodiment for the demand responsive flow controller 10 is illustrated which features a fluidic switch 86 which is characterized by structure which provides "memory" in which the power stream 28 attaches to the wall of the vent port 44 as long as it is unblocked. When the vent port 44 is blocked, the low pressure power stream 28 is deflected through the power stream discharge port 42 for actuating the fluidic valve 30. This arrangement is equally efficient as the arrangement shown in FIG. 2 since the low flow rate control power stream 28 is vented to the atmosphere only during inspiration, which typically accounts for only 30% of the respiration cycle.

As shown in FIG. 3, the diaphragm 50 is disposed in sealing engagement with the vent port 44 which corresponds with expiration by the patient. As the vent port 44 becomes blocked or sealed by the diaphragm, the low pressure power stream 28 is deflected through the power stream discharge port 42 and into the on/off valve control port 66 which combines with the supply pressure to drive the ball 68 into sealing engagement with the lower power flow nozzle seat 76, thereby interrupting flow to the cannula. At the onset of inspiration, the diaphragm 50 is deflected away from the vent port, thereby opening it to atmospheric pressure, and the power stream 28 reverts to the vent port because of its memory feature. This relieves the pressure at the on/off valve control port 66, and allows the ball 68 to move into sealing engagement with the upper power flow nozzle seat 80, thereby closing off the power stream discharge port 42 which reinforces stable flow through the vent port 44.

It will be apparent that the invention may be embodied in other specific forms without departing from the spirit or essential characteristics thereof. Thus the present embodiments should therefore be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by the U.S. Letters Patent is:

1. For use in a respiration system for the administration of oxygen from a supply conduit through a delivery conduit and cannula to a patient, a demand responsive flow controller comprising, in combination:

a flow restrictor adapted to be coupled to the supply conduit for conducting a control power stream;

an on/off fluidic valve having an inlet port adapted to be coupled to the supply conduit, an outlet port adapted to be coupled to the delivery conduit, and a valve control port for closing and opening a fluid flow path between said inlet and outlet ports in response to the application and removal of the control power stream to and from the valve control port, respectively;

a fluidic switch having an inlet port coupled to the output of the flow restrictor, a gate control port for receiving a respiration signal, a discharge port coupled to said valve control port through which the control power stream is conducted only in response to a respiration signal at said control port corresponding with expiration, and a vent port communicating to atmosphere through which the power stream is conducted only in response to a respiration signal at said control port corresponding with inspiration; and, a fluidic transducer adapted to be coupled in fluid communication with the cannula and and including means in movable engagement with the gate control port of the fluidic switch for producing the respiration signals by opening and closing said gate control port to ambient pressure in response to cannula pressure fluctuations corresponding with inspiration and expiration, respectively.

2. The combination as defined in claim 1, said fluidic transducer comprising a housing enclosing a chamber, and wherein said means comprises a flexible diaphragm sealing the chamber and adapted to open and close said gate control port, and a sensor conduit adapted to be connected the chamber in fluid communication with the cannula.

3. The combination as defined in claim 1, including a first check valve connected in series fluid circuit relation between the valve control port and the discharge port of the fluidic switch for conducting the low pressure power stream from the fluidic switch to the on/off valve during expiration and for blocking reverse flow from the on/off fluidic valve to the fluidic switch during inspiration, and a second check valve connected in series fluid circuit relation in said sensor conduit between the on/off fluidic valve and the cannula for conducting the relatively high pressure flow to the patient during inspiration and for blocking reverse flow through the on/off valve during expiration.

4. For use in a respiration system for the administration of oxygen from a supply conduit through a delivery conduit and cannula to a patient, a demand responsive flow controller comprising, in combination:

a flow restrictor adapted to be coupled to the supply conduit for developing a control power stream;

an on/off fluidic valve having an inlet port adapted to be coupled to the supply conduit, an outlet port adapted to be coupled to the delivery conduit, and a valve control port for closing and opening a fluid flow path between said inlet and outlet ports in response to the application and removal of the control power stream to and from the valve control port, respectively;

a fluidic switch having an inlet port coupled to the output of the flow restrictor, a vent port through which the control power stream is conducted when said vent port is open to ambient pressure, and a discharge port connected to said valve control port through which the control power stream is conducted when the vent port is closed to ambient pressure; and, a fluidic tranducer adapted to be coupled in fluid communication with the cannula and including means in movable engagement with the vent port of the fluidic switch for opening and closing the vent port in response to cannula pressure fluctuations corresponding with inspiration and expiration, respectively.

5. The combination as defined in claim 4, said fluidic transducer comprising a housing enclosing a chamber, and wherein said means comprises a flexible diaphragm sealing the chamber adapted to open and close said vent port, and a sensor conduit adapted to connect the chamber in fluid communication with the cannula.

* * * * *